United States Patent [19]

Williams

[11] Patent Number: 5,729,835
[45] Date of Patent: Mar. 24, 1998

[54] PANTY LINER FOR USE WITH THONG UNDERWEAR

[76] Inventor: Magda Williams, 23381 Dome St., Moreno Valley, Calif. 92553

[21] Appl. No.: 792,946

[22] Filed: Jan. 21, 1997

[51] Int. Cl.[6] ............................ A41B 9/00; A41B 9/04; A41B 9/12
[52] U.S. Cl. ............................ 2/406; 2/400; 604/385.1
[58] Field of Search ........................... 2/400, 401, 402, 2/403, 404, 405, 406, 1, 46, 69, 69.5, 73, 53, 104, 54, 55, 56, 57; 450/102, 103, 104; 604/378, 385.1, 389

[56] References Cited

U.S. PATENT DOCUMENTS

| 2,242,937 | 5/1941 | Biederman | 604/378 |
| 3,237,625 | 3/1966 | Johnson | 2/406 |
| 3,613,687 | 10/1971 | Kennedy | 2/406 |
| 4,493,866 | 1/1985 | Kim | 604/378 |
| 4,846,824 | 7/1989 | Lassen et al. | 604/378 |
| 4,856,111 | 8/1989 | Sholes | 2/56 |
| 5,291,617 | 3/1994 | Moretz et al. | 2/406 |
| 5,593,398 | 1/1997 | Weimer | 2/406 |

*Primary Examiner*—Jeanette E. Chapman

[57] ABSTRACT

A panty liner for use with thong underwear including a pliable body portion having a generally oblong configuration. The body portion includes a first end portion of a predetermined width and a second end portion of a predetermined width. The width of the first end portion is greater than the width of the second end portion. The body portion includes a tapered intermediate portion disposed between the first end portion and the second end portion. The body portion is positionable within a pair of thong underwear.

1 Claim, 2 Drawing Sheets

FIG. 3
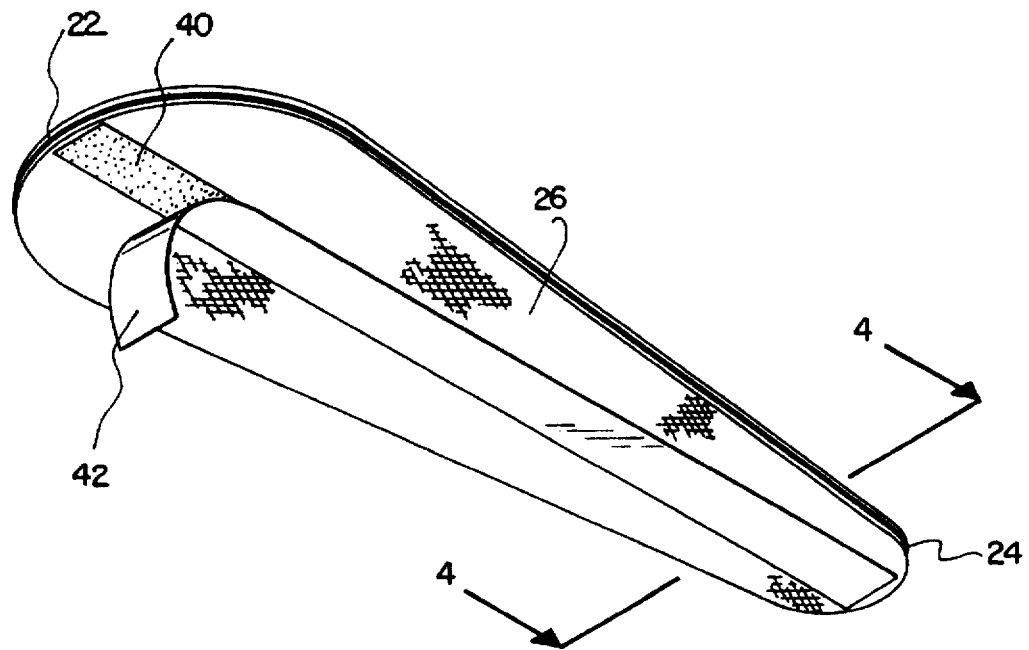
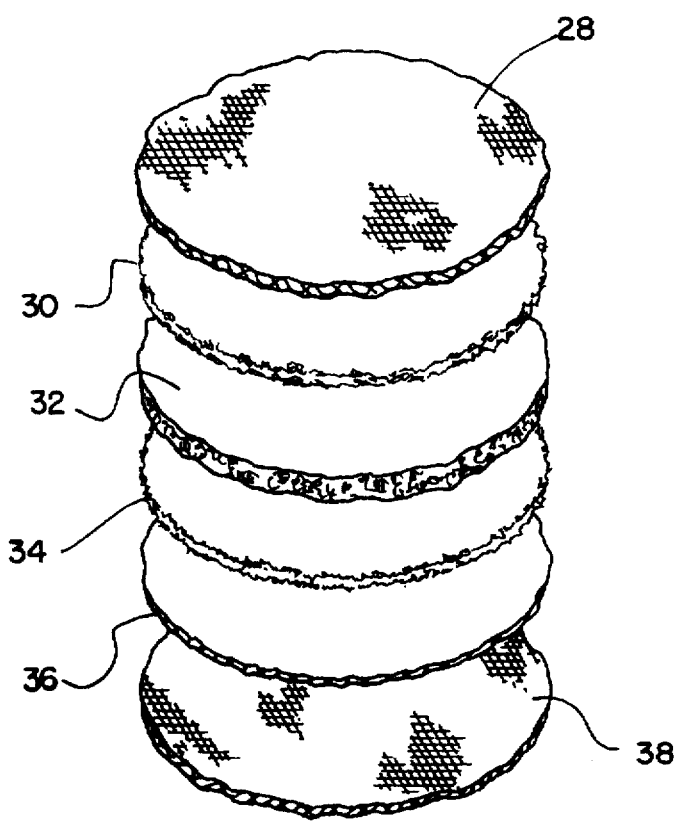
FIG. 4

5,729,835

PANTY LINER FOR USE WITH THONG UNDERWEAR

BACKGROUND OF THE INVENTION

1. Field of the Invention

The present invention relates to a panty liner for use with thong underwear and more particularly pertains to providing protection for a person wearing thong underwear with a panty liner for use with thong underwear.

2. Description of the Prior Art

The use of panty liners is known in the prior art. More specifically, panty liners heretofore devised and utilized for the purpose of absorbing body fluids are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,657,538 to Becker et al. discloses a panty liner with flow retarding layer.

U.S. Pat. No. 4,518,451 to Luceri et al. discloses an embossed panty liner.

U.S. Pat. No. Des. 344,333 to Paddock discloses the ornamental design for a panty liner.

U.S. Pat. No. 4,648,876 to Becker et al. discloses a breathable panty liner.

U.S. Pat. No. Des. 287,637 to Grasso discloses the ornamental design for an embossed panty liner.

U.S. Pat. No. 4,347,092 to Hlaban discloses a panty liner.

While these devices fulfill their respective, particular objective and requirements, the aforementioned patents do not describe a panty liner for use with thong underwear for providing protection for a person wearing thong underwear.

In this respect, the panty liner for use with thong underwear according to the present invention substantially departs from the conventional concepts and designs of the prior art, and in doing so provides an apparatus primarily developed for the purpose of providing protection for a person wearing thong underwear.

Therefore, it can be appreciated that there exists a continuing need for new and improved panty liner for use with thong underwear which can be used for providing protection for a person wearing thong underwear. In this regard, the present invention substantially fulfills this need.

SUMMARY OF THE INVENTION

In the view of the foregoing disadvantages inherent in the known types of panty liners now present in the prior art, the present invention provides an improved panty liner for use with thong underwear. As such, the general purpose of the present invention, which will be described subsequently in greater detail, is to provide a new and improved panty liner for use with thong underwear and method which has all the advantages of the prior art and none of the disadvantages.

To attain this, the present invention essentially comprises a pair of thong underwear having a tapered crotch region. The tapered crotch region includes a wider frontal portion and a narrower posterior portion. The device includes a pliable body portion having a generally oblong configuration. The body portion includes a first end portion of a predetermined width and a second end portion of a predetermined width. The width of the first end portion is greater than the width of the second end portion. The body portion includes a tapered intermediate portion disposed between the first end portion and the second end portion. The body portion includes an upper first layer fabricated of a cotton panel, a second layer fabricated of a cotton weave, a third layer fabricated of an absorbent material, a fourth layer fabricated of a cotton weave, a fifth layer fabricated of a plastic material and a lower sixth layer fabricated of a cotton panel. An outer surface of the lower sixth layer has an adhesive strip disposed thereon. The adhesive strip has a protective backing removably coupled thereto. The body portion is positionable within the tapered crotch region of the pair of thong underwear.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved panty liner for use with thong underwear which has all the advantages of the prior art panty liners and none of the disadvantages.

It is another object of the present invention to provide a new and improved panty liner for use with thong underwear which may be easily and efficiently manufactured and marketed.

It is a further object of the present invention to provide a new and improved panty liner for use with thong underwear which is of durable and reliable construction.

An even further object of the present invention is to provide a new and improved panty liner for use with thong underwear which is susceptible of a low cost of manufacture with regard to both materials and labor, and which accordingly is then susceptible of low prices of sale to the consuming public, thereby making such a panty liner for use with thong underwear economically available to the buying public.

Even still another object of the present invention is to provide a new and improved panty liner for use with thong underwear for providing protection for a person wearing thong underwear.

Lastly, it is an object of the present invention to provide a new and improved panty liner for use with thong underwear including a pliable body portion having a generally oblong configuration. The body portion includes a first end portion of a predetermined width and a second end portion of a predetermined width. The width of the first end portion is greater than the width of the second end portion. The body portion includes a tapered intermediate portion disposed between the first end portion and the second end portion. The body portion is positionable within a pair of thong underwear.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a bottom perspective view of the present invention.

FIG. 4 is a cross-sectional view as taken along line 4—4 of FIG. 3.

The same reference numerals refer to the same parts through the various Figures.

DESCRIPTION OF THE PREFERRED EMBODIMENT

Figure 1:
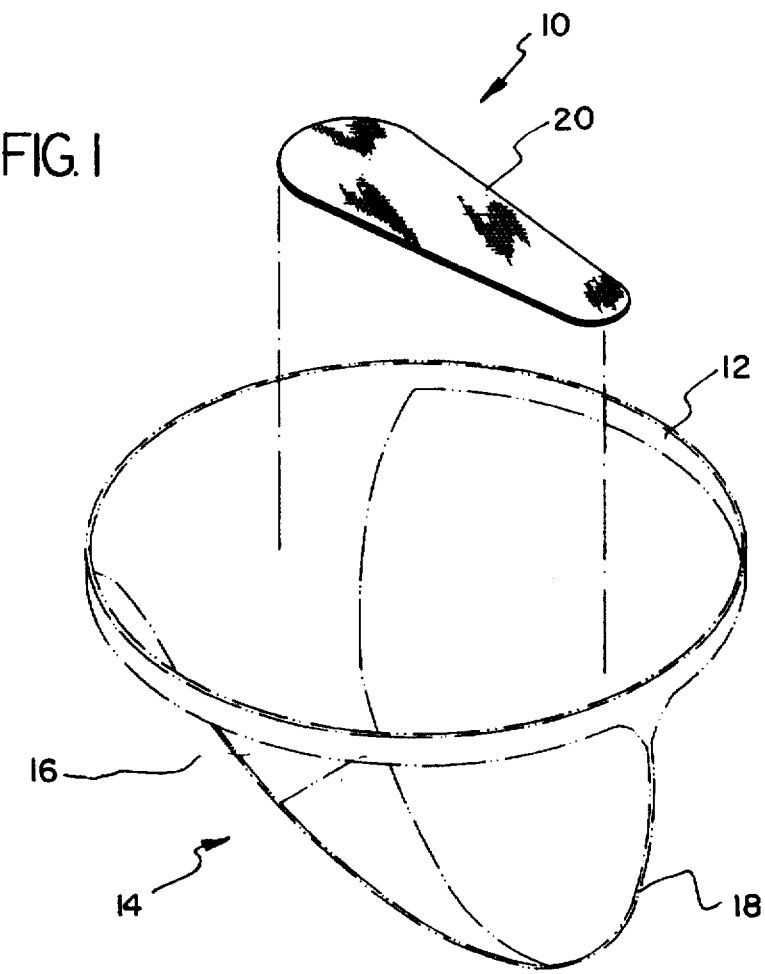
FIG. 1 is a perspective view of the preferred embodiment of the panty liner for use with thong underwear constructed in accordance with the principles of the present invention.

With reference now to the drawings, and in particular, to FIGS. 1 through 4 thereof, the preferred embodiment of the new and improved panty liner for use with thong underwear embodying the principles and concepts of the present invention and generally designated by the reference number 10 will be described.

Specifically, it will be noted in the various Figures that the device relates to a panty liner for use with thong underwear for providing protection for a person wearing thong underwear. In its broadest context, the device consists of a pair of thong underwear and a body portion. Such components are individually configured and correlated with respect to each other so as to attain the desired objective.

The device 10 includes a pair of thong underwear 12 having a tapered crotch region 14. The tapered crotch region 14 includes a wider frontal portion 16 and a narrower posterior portion 18. The pair of thong underwear 12 are best viewed in FIGS. 1 and 2. The thong underwear 12 are like those known in the art and are worn by those who wish not to have panty lines shown through their pants or skirts.

The primary component of the device 10 is the pliable body portion 20. The pliable body portion 20, as bets viewed in FIGS. 2 and 3, has a generally oblong configuration. The body portion 20 includes a first end portion 22 of a predetermined width and a second end portion 24 of a predetermined width. The width of the first end portion 22 is greater than the width of the second end portion 24. The body portion 20 includes a tapered intermediate portion 26 disposed between the first end portion 22 and the second end portion 24.

Now, turning attention to FIG. 4, the body portion 20 includes an upper first layer 28 fabricated of a cotton panel, a second layer 30 fabricated of a cotton weave, a third layer 32 fabricated of an absorbent material, a fourth layer 34 fabricated of a cotton weave, a fifth layer 36 fabricated of a plastic material and a lower sixth layer 38 fabricated of a cotton panel. The layers of the body portion 20 primarily serve as an absorbing means for bodily fluids while at the same time maintaining the dry condition of the underwear 12 as well as comfort of the wearer. The absorbent layer is protected by the first 28 and second layers 30, the second layer 30 will absorb some of the body fluids. Any fluids passing through the absorbent layer will be absorbed by the fourth layer 34 of cotton weave. The fifth layer 36 of plastic will preclude any of the body fluids from reaching the underwear 12.

FIG. 3 illustrates an outer surface of the lower sixth layer 38 having an adhesive strip 40 disposed thereon. The adhesive strip 40 has a protective backing 42 removably coupled thereto.

Figure 2:
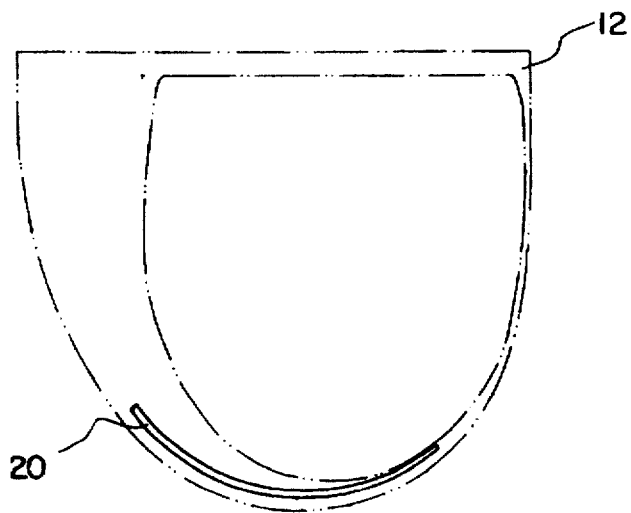
FIG. 2 is a side view of the present invention in place within a pair of thong underwear.

As in FIG. 2, the body portion 20 is positionable within the tapered crotch region 14 of the pair of thong underwear 12. This is simply achieved by removing the protective backing 40 to expose the adhesive strip 38 and placing the body portion 20 within the tapered crotch region 14 of the tapered underwear 12. Removal of the body portion 20 is simple once it has become soiled.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by LETTERS PATENT of the United States is as follows:

1. A panty liner for use with thong underwear for providing protection for a person wearing thong underwear comprising, in combination:

a pair of thong underwear having a tapered crotch region, the tapered crotch region including a wider frontal portion and a narrower posterior portion; and a pliable body portion having a generally oblong configuration, the body portion including a front end portion of a predetermined width and a rear end portion of a predetermined width, the width of the front end portion being greater than the width of the rear end portion, the body portion including a tapered intermediate portion disposed between the front end portion and the rear end portion, the body portion including an upper first layer fabricated of a cotton panel, a second layer fabricated of a cotton weave, a third layer fabricated of an absorbent material, a fourth layer fabricated of a cotton weave, a fifth layer fabricated of a plastic material and a lower sixth layer fabricated of a cotton panel, an outer surface of the lower sixth layer having an adhesive strip disposed thereon, the adhesive strip having a protective backing removably coupled thereto, the body portion positionable within the tapered crotch region of the pair of thong underwear.

* * * * *